(12) United States Patent
Piergallini et al.

(10) Patent No.: US 11,691,025 B2
(45) Date of Patent: *Jul. 4, 2023

(54) METHODS AND COMPOSITIONS FOR REVERSING OR MITIGATING SKIN AGING

(71) Applicant: KLOX TECHNOLOGIES INC., Laval (CA)

(72) Inventors: Remigio Piergallini, Grottammare (IT); Nikolaos Loupis, Athens (GR); Francesco Bellini, Calgary (CA)

(73) Assignee: KLOX TECHNOLOGIES INC., Laval (CA)

( * ) Notice: Subject to any disclaimer, the term of this patent is extended or adjusted under 35 U.S.C. 154(b) by 37 days.

This patent is subject to a terminal disclaimer.

(21) Appl. No.: 17/333,345

(22) Filed: May 28, 2021

(65) Prior Publication Data
US 2021/0283417 A1 Sep. 16, 2021

Related U.S. Application Data

(60) Continuation of application No. 16/693,840, filed on Nov. 25, 2019, now Pat. No. 11,020,609, which is a continuation of application No. 16/210,034, filed on Dec. 5, 2018, now Pat. No. 10,485,986, which is a continuation of application No. 15/162,801, filed on May 24, 2016, now Pat. No. 10,149,985, which is a continuation of application No. 14/540,484, filed on Nov. 13, 2014, now Pat. No. 9,375,446, which is a continuation of application No. 14/137,599, filed on
(Continued)

(51) Int. Cl.
| | |
|---|---|
| *A61K 33/40* | (2006.01) |
| *A61N 5/06* | (2006.01) |
| *A61K 31/352* | (2006.01) |
| *A61K 31/353* | (2006.01) |
| *A61K 31/403* | (2006.01) |
| *A61K 31/4166* | (2006.01) |
| *A61K 31/7008* | (2006.01) |
| *A61K 45/06* | (2006.01) |
| *A01H 5/10* | (2018.01) |
| *A61K 47/18* | (2017.01) |
| *A61K 31/728* | (2006.01) |
| *A61K 41/00* | (2020.01) |
| *A61K 8/22* | (2006.01) |
| *A61K 8/49* | (2006.01) |
| *A61K 8/60* | (2006.01) |
| *A61K 8/73* | (2006.01) |
| *A61Q 19/08* | (2006.01) |
| *A61Q 19/00* | (2006.01) |
| *A61K 47/02* | (2006.01) |
| *A61K 47/22* | (2006.01) |
| *A61K 47/46* | (2006.01) |
| *A61K 31/17* | (2006.01) |
| *A61K 31/404* | (2006.01) |
| *A61K 31/737* | (2006.01) |

(52) U.S. Cl.
CPC ............. *A61N 5/062* (2013.01); *A61K 8/22* (2013.01); *A61K 8/492* (2013.01); *A61K 8/498* (2013.01); *A61K 8/60* (2013.01); *A61K 8/735* (2013.01); *A61K 8/736* (2013.01); *A61K 31/17* (2013.01); *A61K 31/352* (2013.01); *A61K 31/353* (2013.01); *A61K 31/403* (2013.01); *A61K 31/404* (2013.01); *A61K 31/4166* (2013.01); *A61K 31/7008* (2013.01); *A61K 31/728* (2013.01); *A61K 31/737* (2013.01); *A61K 33/40* (2013.01); *A61K 41/0057* (2013.01); *A61K 45/06* (2013.01); *A61K 47/02* (2013.01); *A61K 47/183* (2013.01); *A61K 47/22* (2013.01); *A61K 47/46* (2013.01); *A61N 5/0616* (2013.01); *A61Q 19/00* (2013.01); *A61Q 19/08* (2013.01); *A61N 2005/0662* (2013.01); *A61N 2005/0663* (2013.01)

(58) Field of Classification Search
CPC ............ A61N 5/062; A61N 2005/0663; A61K 45/06; A61K 31/737; A61K 31/352; A61K 31/353; A61K 31/403; A61K 31/4166; A61K 31/7008; A61K 31/728; A61K 33/40; A61K 41/0057; A61K 31/404; A61K 47/46; A61K 8/736; A61K 47/183; A61K 47/02; A61K 47/22; A61K 31/17; A61K 8/735; A01H 5/10; A61Q 19/00

See application file for complete search history.

(56) References Cited

U.S. PATENT DOCUMENTS

| | | | |
|---|---|---|---|
| 2,877,221 | A | 3/1959 | Lanbach |
| 3,293,127 | A | 12/1966 | Beck |

(Continued)

FOREIGN PATENT DOCUMENTS

| | | |
|---|---|---|
| CA | 2222027 | 6/1998 |
| CA | 2360202 | 12/1999 |

(Continued)

OTHER PUBLICATIONS

The Search Report issued in corresponding application 201610020876.1 from China's National Intellectual Property Administration (CNIPA) dated Jan. 14, 2019.

(Continued)

*Primary Examiner* — Hasan S Ahmed
(74) *Attorney, Agent, or Firm* — BCF LLP

(57) ABSTRACT

A method for reversing or mitigating skin aging comprising topically applying a composition which comprises at least one oxidant, and at least one fluorescent dye capable of activating the oxidant and illuminating said composition for a time sufficient to activate the at least one oxidant.

9 Claims, 3 Drawing Sheets

Related U.S. Application Data

Dec. 20, 2013, now Pat. No. 8,911,791, which is a continuation of application No. 13/770,907, filed on Feb. 19, 2013, now Pat. No. 8,637,086, which is a division of application No. 13/127,445, filed as application No. PCT/CA2009/001615 on Nov. 6, 2009, now Pat. No. 8,658,219.

(60) Provisional application No. 61/112,235, filed on Nov. 7, 2008.

(56) References Cited

U.S. PATENT DOCUMENTS

| | | |
|---|---|---|
| 3,309,274 A | 3/1967 | Brilliant |
| 3,372,125 A | 3/1968 | Hill |
| 3,595,798 A | 7/1971 | Smith et al. |
| 3,597,362 A | 8/1971 | Rauhut et al. |
| 3,652,420 A | 3/1972 | Hill |
| 3,671,450 A | 6/1972 | Rauhut et al. |
| 3,728,446 A | 4/1973 | Roberts et al. |
| 4,574,097 A | 3/1986 | Honeycutt |
| 4,846,165 A | 7/1989 | Hare et al. |
| 4,891,211 A | 1/1990 | Winston |
| 4,992,256 A | 2/1991 | Skaggs et al. |
| 5,599,342 A | 2/1997 | Hsia et al. |
| 5,658,148 A | 8/1997 | Neuberger et al. |
| 5,749,968 A | 5/1998 | Melanson et al. |
| 5,785,527 A | 7/1998 | Jensen et al. |
| 5,844,016 A | 12/1998 | Sawhney et al. |
| 5,858,332 A | 1/1999 | Jensen et al. |
| 5,922,331 A | 7/1999 | Mausner |
| 5,977,199 A | 11/1999 | Xie |
| 6,030,222 A | 2/2000 | Tarver |
| 6,036,493 A | 3/2000 | Sharma |
| 6,056,548 A | 5/2000 | Neuberger et al. |
| 6,084,005 A | 7/2000 | Fukunishi et al. |
| 6,107,466 A | 8/2000 | Hasan et al. |
| 6,121,341 A | 9/2000 | Sawhney et al. |
| 6,149,895 A | 11/2000 | Kutsch |
| 6,162,055 A | 12/2000 | Montgomery et al. |
| 6,254,388 B1 | 7/2001 | Yarborough |
| 6,267,976 B1 | 7/2001 | Barnhart et al. |
| 6,337,357 B1 | 1/2002 | Fukunishi et al. |
| 6,343,933 B1 | 2/2002 | Montgomery et al. |
| 6,365,134 B1 | 4/2002 | Orlowski et al. |
| 6,387,353 B1 | 5/2002 | Jensen et al. |
| 6,391,283 B1 | 5/2002 | Jensen et al. |
| 6,420,455 B1 | 7/2002 | Landgrebe et al. |
| 6,423,697 B1 | 7/2002 | Friedman |
| 6,440,396 B1 | 8/2002 | McLaughlin |
| 6,444,725 B1 | 9/2002 | Trom et al. |
| 6,475,497 B1 | 11/2002 | Rajaiah et al. |
| 6,485,709 B2 | 11/2002 | Banerjee et al. |
| 6,488,914 B2 | 12/2002 | Montgomery |
| 6,514,543 B2 | 2/2003 | Montgomery |
| 6,528,555 B1 | 3/2003 | Nikutowski et al. |
| 6,536,628 B2 | 3/2003 | Montgomery |
| 6,541,460 B2 | 4/2003 | Petito |
| 6,558,653 B2 | 5/2003 | Andersen et al. |
| 6,846,182 B1 | 1/2005 | Sibner |
| 6,905,672 B2 | 6/2005 | Rajaiah et al. |
| 6,960,079 B2 | 11/2005 | Brennan et al. |
| 7,066,941 B2 | 6/2006 | Perricone |
| 7,081,128 B2 | 7/2006 | Hart et al. |
| 7,114,953 B1 | 10/2006 | Wagner |
| 7,220,438 B2 | 5/2007 | Quintanilla Almagro et al. |
| 7,314,470 B2 | 1/2008 | Malodobry |
| 7,354,448 B2 | 4/2008 | Altshuler et al. |
| 8,075,875 B2 | 12/2011 | Piergallini et al. |
| 8,182,473 B2 | 5/2012 | Altshuler et al. |
| 8,632,822 B2 | 1/2014 | Piergallini et al. |
| 8,637,086 B2 | 1/2014 | Piergallini et al. |
| 8,658,219 B2 | 2/2014 | Piergallini et al. |
| 8,685,466 B2 | 4/2014 | Piergallini et al. |
| 8,911,791 B2 | 12/2014 | Piergallini et al. |
| 8,974,833 B2 | 3/2015 | Piergallini et al. |
| 8,986,719 B2 | 3/2015 | Piergallini et al. |
| 8,986,745 B2 | 3/2015 | Piergallini et al. |
| 8,986,746 B2 | 3/2015 | Piergallini et al. |
| 9,345,648 B2 | 5/2016 | Piergallini et al. |
| 2001/0022970 A1 | 9/2001 | Dees et al. |
| 2003/0133940 A1 | 7/2003 | Dees et al. |
| 2003/0198605 A1 | 10/2003 | Montgomery |
| 2004/0136971 A1 | 7/2004 | Scharp et al. |
| 2004/0191330 A1 | 9/2004 | Keefe et al. |
| 2004/0262569 A1 | 12/2004 | Cho et al. |
| 2005/0020696 A1 | 1/2005 | Montgomery et al. |
| 2005/0026298 A1 | 2/2005 | Bickett et al. |
| 2005/0042712 A1 | 2/2005 | Huth et al. |
| 2005/0049228 A1 | 3/2005 | Albrecht et al. |
| 2005/0059731 A1 | 3/2005 | Albrecht et al. |
| 2005/0098766 A1 | 5/2005 | Watson |
| 2005/0123588 A1 | 6/2005 | Zhu et al. |
| 2006/0099155 A1 | 5/2006 | MacDonald et al. |
| 2006/0198796 A1 | 9/2006 | Giniger et al. |
| 2006/0287211 A1 | 12/2006 | Barbizan et al. |
| 2007/0092469 A1 | 4/2007 | Jacobs |
| 2007/0128132 A1 | 6/2007 | Piergallini et al. |
| 2007/0166369 A1 | 7/2007 | Neuberger et al. |
| 2007/0191249 A1 | 8/2007 | Lant |
| 2007/0244195 A1 | 10/2007 | Buckhart et al. |
| 2008/0058689 A1 | 3/2008 | Holloway et al. |
| 2008/0108681 A1 | 5/2008 | Scimeca et al. |
| 2008/0113037 A1 | 5/2008 | Green et al. |
| 2008/0206159 A1 | 8/2008 | Tamarkin et al. |
| 2008/0255498 A1 | 10/2008 | Houle |
| 2008/0305101 A1 | 12/2008 | Ruoslahti et al. |
| 2010/0266989 A1 | 10/2010 | Piergallini et al. |
| 2011/0218482 A1 | 9/2011 | Piergallini et al. |
| 2011/0224599 A1 | 9/2011 | Piergallini et al. |
| 2014/0303547 A1 | 9/2014 | Loupis et al. |

FOREIGN PATENT DOCUMENTS

| | | |
|---|---|---|
| CA | 2457590 | 8/2002 |
| CA | 2551613 | 12/2005 |
| CA | 2580381 | 1/2006 |
| CA | 2809405 | 1/2012 |
| CN | 1607946 A | 4/2005 |
| CN | 1744821 A | 3/2006 |
| CN | 104707143 B | 4/2018 |
| EP | 0356868 | 3/1990 |
| EP | 0380157 | 8/1990 |
| EP | 0704539 | 4/1996 |
| EP | 1235543 | 9/2002 |
| EP | 1235544 | 9/2002 |
| EP | 1749532 | 2/2007 |
| EP | 1779891 | 5/2007 |
| EP | 1951184 | 8/2008 |
| EP | 2338465 | 6/2011 |
| JP | 01-279838 | 10/1989 |
| JP | 2002-233612 | 9/1990 |
| JP | H3169805 | 7/1991 |
| JP | 04-219756 | 8/1992 |
| JP | H10182390 | 7/1998 |
| JP | H10330235 | 12/1998 |
| JP | H092925 | 1/1999 |
| JP | 2000-053550 | 2/2000 |
| JP | 2001-511137 | 8/2001 |
| JP | 2002-502864 | 1/2002 |
| JP | 2002-226349 | 8/2002 |
| JP | 2002-293747 | 10/2002 |
| JP | 2003-339875 | 12/2003 |
| KR | 10-1835047 | 3/2018 |
| WO | 1981000513 | 3/1981 |
| WO | 1990009779 | 9/1990 |
| WO | 1991002530 | 3/1991 |
| WO | 1997021420 | 6/1997 |
| WO | 1998010738 | 3/1998 |
| WO | 1998011827 | 3/1998 |
| WO | 1998023219 | 6/1998 |
| WO | 1998030169 | 7/1998 |
| WO | 1998033761 | 8/1998 |
| WO | 1998036700 | 8/1998 |

(56) References Cited

FOREIGN PATENT DOCUMENTS

| | | |
|---|---|---|
| WO | 1999039238 | 8/1999 |
| WO | 1999040870 | 8/1999 |
| WO | 1999049823 | 10/1999 |
| WO | 1999063900 | 12/1999 |
| WO | 2000040266 | 7/2000 |
| WO | 2001000190 | 1/2001 |
| WO | 2001012181 | 2/2001 |
| WO | 2002022097 | 3/2002 |
| WO | 2002087642 | 11/2002 |
| WO | 2003000215 | 1/2003 |
| WO | 2003017824 | 3/2003 |
| WO | 2003061696 | 7/2003 |
| WO | 2003099247 | 12/2003 |
| WO | 2004028498 | 4/2004 |
| WO | 2004073540 | 9/2004 |
| WO | 2004081222 | 9/2004 |
| WO | 2005009604 | 2/2005 |
| WO | 2005051305 | 6/2005 |
| WO | 2005112948 | 12/2005 |
| WO | 2006014597 | 2/2006 |
| WO | 2006032847 | 3/2006 |
| WO | 2006047868 | 5/2006 |
| WO | 2006072243 | 7/2006 |
| WO | 2006125650 | 11/2006 |
| WO | 2006135344 | 12/2006 |
| WO | 2007087259 | 2/2007 |
| WO | 2007025244 | 3/2007 |
| WO | 2007080453 | 7/2007 |
| WO | 2008011707 | 1/2008 |
| WO | 2008013962 | 1/2008 |
| WO | 2008052081 | 5/2008 |
| WO | 2008096182 | 8/2008 |
| WO | 2009089346 | 7/2009 |
| WO | 2010051636 | 5/2010 |
| WO | 2010051641 | 5/2010 |
| WO | 2011006263 | 1/2011 |
| WO | 2011058448 | 5/2011 |
| WO | 2011134087 | 11/2011 |
| WO | 2012011875 | 1/2012 |
| WO | 2013155620 | 10/2013 |
| WO | 2014040176 | 3/2014 |

OTHER PUBLICATIONS

English abstract for CN1607946A.
English abstract for CN1744821A.
English abstract for CN104707143B.
Alster et al., "Photodynamic therapy: practical cosmetic applications", Journal of Drugs in Dermatology, 5(8):764-768 (2006).
Antunes et al., "Evaluation of the clastogenicity and anticlastogenicity of the carotenoid bixin in human lymphocyte cultures", Mutation Research, 585(1-2): 113-9 (2005).
Ariizumi et al., "Clinical Evaluation of a Topical Applicant TSG-88 for Periodontal Diseases", Dental Drug Therapy, 10(2):157-168 (1991).
Berneburg et al., "Phototherapy with narrowband UVB", Acta Dermato-Venereologica, 85:1-11 (2005).
Chen et al., "Study of the chemiluminescent characteristics of some xanthone dyes", Analytica Chimica Acta, 292(1-2):159-167 (1994).
Colman et al., "The healing of wounds in the skin of piglets treated with benzoyl peroxide", The Journal of Dermatologic Surgery and Oncology, 4(9):705-707 (1978).
Darzynkiewicz et al., "Photosensitizing effects on the tricyclic heteroaromatic cationic dyes pyronin Y and toluidine blue O (tolonium chloride)", Cancer Research, 48(5):1295-1299 (1988).
De et al., "Environmental effects on the aggregation of some xanthene dyes used in lasers", Spectrochimica Acta Part A: Molecular and Biomolecular Spectroscopy, 61(8):1821-1833 (2005).
Decraene et al., "Cellulose Acetate Containing Toluidine Blue and Rose Bengal Is an Effective Antimicrobial Coating When Exposed to White Light", Applied and Env. Microbiology, 72:6, 4436-4439 (Jun. 2006).

European Supplemetary Search Report, Application No. EP09824320, dated Mar. 28, 2012 (12 pages).
FDA, Color Additive Status List, http://www.cfsanJda.gov/-dms/opa-appc.html, downloaded Jun. 18, 2008 (13 pages).
FDA, Product Classification Database Search, http://www.accessdata.fda.gov/scripts/cdrh/cfdocs/cfpcd/classification/c.f?ID-3964, Device: Eosin y: database, downloaded Jun. 18, 2008 (2 pages).
Fisher Scientific, "Material Safety Data Sheet: Sodium acetate buffer", https://fscimagef.fishersci.com/msds/91502.htm (ACC #91502) (Apr. 13, 2000) (5 pages).
Golberg, "Photodynamic therapy in skin rejuvenation", Clinics in Dermatology, 26(6):608-613 (2008).
Jankowski et al., "The action of photosensitizers and serum in a bactericidal process. II. The effects of dyes: hypericin, eosin Y and saphranine O", Polish Journal of Microbiology, 54(4):323-330 (2005).
Kelly et al., "Cobined photodynamic and photodermal induced injury enhances damage to in vivo model blood vessels", Laser in Surgery and Medicine, 34(5):407-413 (2004).
McCullach et al., "Photosensitized destruction of Chlorella vulgaris by methylene blue or nuclear fast red combined with hydrogen peroxide under visible light irradiation", Environmental Science and Technology, 40(7):2421-2425 (2006).
Meisel et al., "Photodynamic therapy for periodontal diseases: State of the art", Journal of Photochemistry and Photobiology B: Biology, 79:159-170 (2005).
Mintel, "Active Plus Deep Cleaning Tablets", Database GNPD [Online], May 2007, XP002769877, Database accession No. 707777 *Ingredients*.
Mintel, "Effervescent Tablets", Database GNPD [Online] May 2009, XP002769876, Database accession No. 1089966 *Ingredients*.
Mintel, "Teen Braces Cleaner", http://gnpd.com, Jan. 2014 (2 pages).
Montenegro et al., "Model studies on the photosensitized isomerization of bixin", Journal of Agriculture and Food Chemistry, 52(2): 367-73 (2004).
Nolan et al., "The efficacy of topical hyaluronic acid in the management of oral lichen planus", Journal of Oral Pathology and Medicine, 38(3):299-303 (2006).
Nolan et al., "The efficacy of topical hyaluronic acid in the management of recurrent aphthous ulceration", Journal of Dral Pathology and Medicine, 35:461-465 (2006).
PCT International Search Report and Written Opinion for International Serial No. PCT/GR2007/000006, dated Oct. 12, 2007 (8 pages).
PCT International Search Report and Written Opinion for International Serial No. PCT/IB2006/004034, dated Sep. 20, 2007 (13 pages).
PCT International Search Report for International Serial No. PCT/CA2009/001615, dated Feb. 9, 2010 (9 pages).
Publication date of following document established by Internet Archive Wayback Machine (3 pages)<URL: <http://web.archive.org/web/20090208211504/http://en.wikipedia.org/wiki/Eosin Aug. 2, 2009.
Resources:Fluorochrome Absorption Emission Wavelenghts [Online] XP002449595 Retrived from the Internet: URL: http://www.sciencegateway.org/resources/fae1.htm>[retrieved on Sep. 6, 2007] see p. 2: Rhodamine WT emission nm 555 p. 2 (12 pages).
Rodgers, William, "Fluorescence Polarization Standards for High-Throughput Screening and Imaging", Bio Techniques, vol. 32, pp. 34-42 (2002).
Roy et al., "Dermal Wound Healing is Subject to Redox Control", Molecular Therapy, 13(1):211-220 (2006).
Sezer et al., "Topical Drug Delivery Using Chitosan Nano- and Microparticles", Expert Opinion in Drug Delivery, Informa UK, 9(9):1129-1146 (2012).
Steinberg et al., "Genetic and Physiological Effects of Noncoherent Visible Light Combined with Hydrogen Peroxide on *Streptococcus mutans* in Biofilm", Antimicrobial Agentsand Chemotherapy, 52(7):2626-2631 (2008).

(56) References Cited

OTHER PUBLICATIONS

Subba et al., "Photocatalytic transformation of dyes and by-products in the presence of hydrogen peroxide", Environmental Technology, 24(8):1025-1030 (2003).

Sun, "Lasers and Light Amplification in Dentistry", retrieved online at http://www.sundds.comllaser/, downloaded Jun. 23, 2005 (14 pages).

Thompson et al., "Fluorescence Polarization Standards for High-Throughput Screening and Imaging", Bio Techniques, 32:34-42 (2002).

METHODS AND COMPOSITIONS FOR REVERSING OR MITIGATING SKIN AGING

CROSS-REFERENCE TO RELATED APPLICATIONS

This application is a continuation of U.S. patent application Ser. No. 16/693,840 filed on Nov. 25, 2019, now U.S. Pat. No. 11,020,609, which is a continuation of U.S. patent application Ser. No. 16/210,034, filed on Dec. 5, 2018, now U.S. Pat. No. 10,485,986, which is a continuation of U.S. patent application Ser. No. 15/162,801, filed May 24, 2016 and now U.S. Pat. No. 10,149,985, which is a continuation of U.S. patent application Ser. No. 14/450,484, filed Nov. 13, 2014 and now U.S. Pat. No. 9,375,446, which is a continuation of U.S. patent application Ser. No. 14/137,599, filed Dec. 20, 2013 and now U.S. Pat. No. 8,911,791, which is a continuation of U.S. patent application Ser. No. 13/770,907, filed Feb. 19, 2013 and now U.S. Pat. No. 8,687,086, which is a divisional of U.S. patent application Ser. No. 13/127,445, filed on May 3, 2011 and now U.S. Pat. No. 8,658,219, which is a national stage filing under 35 U.S.C. § 371 of International Application No. PCT/CA2009/001615, filed on Nov. 6, 2009, which claims the benefit of the filing date under 35 U.S.C. § 119(e) to U.S. Provisional Application 61/112,235, filed on Nov. 7, 2008, the disclosure of which are hereby incorporated by reference in their entireties. International Application No. PCT/CA2009/001615 was published under PCT Article 21(2) in English.

BACKGROUND

(a) Field

The subject matter disclosed generally relates to a skin rejuvenation composition and method of treatments thereof.

(b) Related Prior Art

The application of non-ablative skin rejuvenation to repair, or offset, the results of both chronological- and photo-ageing in the skin of the face, neck, hands and exposed areas of the body has become extremely popular. From the original mechanical and chemical peels, clinicians rapidly adopted the use of ablative skin rejuvenation using lasers, albeit with the negative effects of severe morbidity (erythema and edema) resulting in patient downtime. These disadvantages significantly offset the good results of the treatment. Photorejuvenation techniques such as lasers and intense pulsed light (IPL) sources were then developed to deliver thermal damage to the dermis under cooling, termed non-ablative, skin rejuvenation. This generally localised thermal damage to the deeper layers of the skin (dermis) whilst the forced cooling helped to protect the upper (and therefore highly visible) layers from thermal damage. Laser ablative skin resurfacing has been a popular modality for the removal or improvement of major wrinkles and other severe symptoms of aging. The principles of ablative therapy are based on light-tissue interaction delivering the optimum amount of controlled residual thermal damage with precise epidermal ablation, therefore invoking a wound response and thus maximizing the clinical result whilst minimizing side effects and their associated downtime. Unfortunately, the resulting crusting, oedema and long-term erythema are major stumbling blocks for all but the most determined patient.

Photodynamic therapy of the skin using photoactive dyes such as Erythrosine B, Safranin O has been employed to destroy bacteria, as described in WO 05/032459 and WO 05/021094, both to Albrecht et al. The photoactive dyes are employed to directly destroy bacteria. The compositions described in these patent applications lack oxidants and healing factors, and they are not employed for directly promoting skin rejuvenation.

Hence, there is a need to accelerate and/or improve rejuvenation of the skin following invasive or non-invasive treatment. Accelerated recovery offers enhanced patient safety (e.g. a reduced window for infection and pain) as well as fitting with the trend towards less aggressive and less invasive treatments.

Therefore, it would be highly desirable to be provided with a novel composition for the rejuvenation of skin damages in order to improve a patient's skin condition and accelerate the healing process following the establishment of lesions caused by chronological ageing and photo-ageing.

SUMMARY

In accordance with one embodiment there is disclosed a skin rejuvenation composition which comprises at least one oxidant, at least one photoactivator capable of activating the oxidant, and at least one healing factor chosen from hyaluronic acid, glucosamine and allantoin, in association with a pharmaceutically acceptable carrier.

The oxidants may be chosen from hydrogen peroxide, carbamide peroxide and benzoyl peroxide.

The skin rejuvenation composition may further comprise at least one hydrophilic gelling agent.

The hydrophilic gelling agent may be chosen from glucose, modified starch, methyl cellulose, carboxymethyl cellulose, propyl cellulose, hydroxypropyl cellulose, Carbopol® polymers, alginic acid, sodium alginate, potassium alginate, ammonium alginate, calcium alginate, agar, carrageenan, locust bean gum, pectin, gelatin.

The photoactivators may be chosen from a xanthene derivative dye, an azo dye, a biological stain, and a carotenoid.

The xanthene derivative dye may be chosen from a fluorene dye, a fluorone dye, and a rhodole dye.

The fluorene dye may be chosen from a pyronine dye and a rhodamine dye.

The pyronine dye may be chosen from pyronine Y and pyronine B.

The rhodamine dye may be chosen from rhodamine B, rhodamine G and rhodamine WT.

The fluorone dye may be chosen from fluorescein and fluorescein derivatives.

The fluorescein derivative may be chosen from phloxine B, rose bengal, and merbromine.

The fluorescein derivative may be chosen from eosin and erythrosine.

The azo dye may be chosen from methyl violet, neutral red, para red, amaranth, carmoisine, allura red AC, tartrazine, orange G, ponceau 4R, methyl red, and murexide-ammonium purpurate.

The biological stain may be chosen from saffranin O, basic fuchsin, acid fuschin, 3,3' dihexylocarbocyanine iodide, carminic acid, and indocyanine green.

The carotenoid may be chosen from crocetin, α-crocin (8,8-diapo-8,8-carotenoic acid), zeaxanthine, lycopene, α-carotene, β-carotene, bixin, and fucoxanthine.

The carotenoid may be present in the composition as a mixture chosen from saffron red powder, annatto extract and brown algae extract.

The skin rejuvenation composition may further comprise at least one chelating agent.

The chelating agent may be chosen from ethylenediaminetetraacetic acid (EDTA) and ethylene glycol tetraacetic acid (EGTA).

The skin rejuvenation composition may further comprise at least one lipolysis stimulating factor.

The lipolysis stimulating factor may be chosen from caffeine and paraxanthine.

In accordance with one embodiment, there is disclosed a method for skin rejuvenation which comprises the steps of a) topically applying on a patient's skin a composition comprising at least one oxidant, at least one photoactivator capable of activating the oxidant; and b) treating said skin of step a) to actinic light for a time sufficient for said photoactivator to cause activation of said oxidant.

The method for skin rejuvenation may comprise exposing the skin to actinic light for a period of about 60 seconds to about 5 minutes.

The method for skin rejuvenation may comprise exposing the skin to actinic light for a period of about 60 seconds to about 5 minutes per $cm^2$ of an area to be treated.

The method for skin rejuvenation may comprise exposing the skin to a source of actinic light that is in continuous motion over the area being treated.

The method for skin rejuvenation may comprise exposing the skin to actinic light that may be visible light having a wavelength between 400 nm and 600 nm.

The following terms are defined below.

The term "hydrophilic gelling agent" is intended to mean a material that thickens and stabilizes liquid solutions, emulsions, and suspensions. Hydrophillic gelling agents dissolve in liquid and provide a structure giving the resulting gel an appearance of a solid matter, while being mostly composed of a liquid. Hydrophillic gelling agents are very similar to thickeners.

The term "actinic light" is intended to mean light energy emitted from a specific light source (lamp, LED, or laser) and capable of being absorbed by matter (e.g. the photoactivator defined below) and produce an identifiable or measurable change when it interacts with it; as clinically identifiable change we can presume a change in the color of the photoactivator used (e.g. from red to transparent).

The term "photoactivator" is intended to mean a chemical compound capable of absorbing actinic light. The photoactivator readily undergoes photoexcitation and then transfers its energy to other molecules, thus enhancing or accelerating the dispersion of light, and enhancing or activating the oxidant present in the reaction mixture.

The term "oxidant" is intended to mean a either a chemical compound that readily transfers oxygen atoms and oxidize other compounds, or a substance that gains electrons in a redox chemical reaction.

The term "chelating agent" is intended to mean a chemical that removes metal ions, such as iron, and holds them in solution.

The term "healing factor" is intended to mean a compound that promotes or enhances the healing or regenerative process of a tissue.

The term "lipolysis" is intended to mean the process in which lipids are broken down into their constituent fatty acids.

The term "time of exposure to actinic light" is intended to mean the time a tissue, skin or wound is exposed to actinic light per application of actinic light.

The term "total time of exposure to actinic light" is intended to mean the cumulative time a tissue, skin or wound is exposed to actinic light after several application of actinic light.

The term "pharmaceutically acceptable carrier" is intended to mean a preservative solution, a saline solution, an isotonic (about 0.9%) saline solution, or about a 5% albumin solution, suspension, sterile water, phosphate buffered saline, and the like. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

The term "rejuvenation" is intended to mean is the reversal or mitigation of the aging process, or any other processes (e.g. abrasion caused by a fall, burns, etc.) that may have damaged or caused an accumulation of damage to macromolecules, cells, tissues and organs, including the skin. Rejuvenation is the repair of any of such damage.

The term "photorejuvenation" is intended to mean the use of light for the reversal or mitigation of the aging process, or any other processes (e.g. abrasion caused by a fall, burns, etc.) that may have damaged or caused an accumulation of damage to macromolecules, cells, tissues and organs, including the skin.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION OF THE PREFERRED EMBODIMENTS

Figure 1:
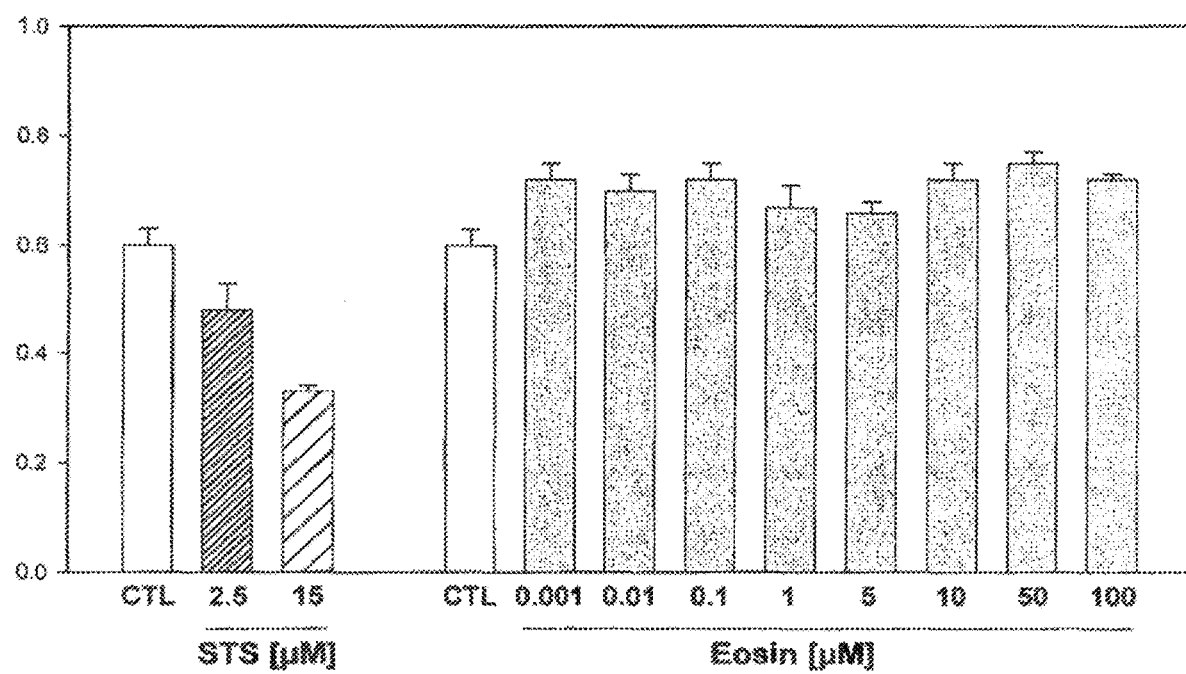
FIG. 1 illustrates that Eosin Y does not affect cellular viability. Hep G2 cells were treated for 24 hours with increasing concentrations (0.001 to 100 μM) of Eosin Y, or left untreated (CTL). Staurosporine (STS) was used as a positive control inducing cellular mortality. Higher concentrations (0.5 and 1 mM) of Eosin Y could not be tested as the dye interfered with the assay.

In accordance with one embodiment, there is provided a skin rejuvenation composition and the method of use of the composition on a patient's skin. This product accelerate rejuvenation of a skin.

In accordance with another embodiment, there is provided a method of use of the composition that is a photodynamic technique whereby the composition is activated by light, providing a beneficial effect on the skin and promoting rejuvenation.

The composition and method may be used to treat damages caused by normal temporal aging, as well as premature aging of the skin caused by exposure to the sun. These damages include but are not limited to photo-aging, hyperpigmentation, large pores, skin irregularities, fine lines, dark skin discoloration, sun damage, pigmented lesions (e.g. melanocytic proliferations, reticular melanotic hypermelanoses), hyperpigmented lesions (e.g. post-traumatic hyperpigmentation), wrinkles, sagging skin, and scars.

It may also be used to treat a wide array of skin conditions. These include but are not limited to acne and acne scars, rosacea. Nevi (blemish on the skin), Mongolian spots, such as Becker's nevus, blue nevus, congenital nevus, pigmented nevus (mole), nevus of Ota and Ito, pigmented spindle cell nevus, and dysplastic nevus may also be treated with the composition.

Visible vascular lesions to the skin may also be treated with the composition. These include but are not limited to matted telangiectasia, lentigines, cherry angioma (a.k.a. "De Morgan spots," and "Senile angiomas"), spider angioma (a.k.a. nevus araneus, spider nevus, or vascular spider), vascular lesions such as vascular birthmarks, blue, red or purple port wine stains, red or blue facial and leg veins (a.k.a. spider veins). The composition and method may be used to help in the removal of most tattoos.

The composition comprises a number of active principles selected from groups of possible components. These various active principles each have their mechanism of action.

Oxidants

The composition comprises oxidants as a source of oxygen radicals. Peroxide compounds are oxidants that contain the peroxy group (R—O—O—R), which is a chainlike structure containing two oxygen atoms, each of which is bonded to the other and a radical or some element. Suitable oxidants for preparation of the active medium include, but are not limited to:

Hydrogen peroxide ($H_2O_2$) is the starting material to prepare organic peroxides. $H_2O_2$ is a powerful oxidizing agent, and the unique property of hydrogen peroxide is that it breaks down into water and oxygen and does not form any persistent, toxic residual compound. Hydrogen peroxide for use in this composition can be used in a gel, for example with 6% hydrogen peroxide. A suitable range of concentration over which hydrogen peroxide can be used in the present composition is from about 3.5% to about 6%.

Urea hydrogen peroxide (also known as urea peroxide, carbamide peroxide or percarbamide) is soluble in water and contains approximately 35% hydrogen peroxide. Carbamide peroxide for use in this composition can be used as a gel, for example with 16% carbamide peroxide that represents 5.6% hydrogen peroxide. A suitable range of concentration over which urea peroxide can be used in the present composition is from about 10% to about 16%. Urea peroxide brakes down to urea and hydrogen peroxide in a slow-release fashion that can be accelerated with heat or photochemical reactions. The released urea [carbamide, $(NH_2)CO_2)$], is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. It is found in treatments for acne, in concentrations varying from 2.5% to 10%. The released peroxide groups are effective at killing bacteria. Benzoyl peroxide also promotes skin turnover and clearing of pores, which further contributes to decreasing bacterial counts and reduce acne. Benzoyl peroxide breaks down to benzoic acid and oxygen upon contact with skin, neither of which are toxic. A suitable range of concentration over which benzoyl peroxide can be used in the present composition is from about 2.5% to about 5%.

Inclusion of other forms of peroxides (e.g. organic or inorganic peroxides) should be avoided due to their increased toxicity and their unpredictable reaction with the photodynamic energy transfer.

Photoactivators:

The photoactivators transfer light energy to the oxidants. Suitable photoactivators can be fluorescent dyes (or stains), although other dye groups or dyes (biological and histological dyes, food colorings, carotenoids) can also be used. Combining photoactivators may increase photo-absorption by the combined dye molecules and enhance absorption and photo-biomodulation selectivity. This creates multiple possibilities of generating new photosensitive, and/or selective photoactivator mixtures.

An advantageous characteristic of a photoactivator is increased fluorescence. In the present invention, re-emission of light in the green to yellow spectrum would be advantageous, since it is a deep penetrating wavelength range, with deep absorption by the blood. This confers a strong increase on the blood flow, vasodilatation and angiokinetic phenomena. Suitable photoactivators include, but are not limited to:

Xanthene Derivatives:

The xanthene derivative dyes have been used and tested for a long time worldwide. They display low toxicity and increased fluorescence. The xanthene group consists of 3 sub-groups that are: a) the fluorenes; b) fluorones; and c) the rhodoles.

The fluorenes group comprises the pyronines (e.g. pyronine Y and B) and the rhodamines (e.g. rhodamine B, G and WT). Depending on the concentration used, both pyronines and rhodamines may be toxic and their interaction with light may lead to increased toxicity. Similar effects are known to occur for the rhodole dye group.

The fluorone group comprises the fluorescein dye and the fluorescein derivatives.

Fluorescein is a fluorophore commonly used in microscopy with an absorption max. of 494 nm and an emission max. of 521 nm. The disodium salt of fluorescein is known as D&C Yellow 8. It has very high fluorescence but photodegrades quickly. In the present composition, mixtures of fluorescein with other photoactivators such as indocyanin green and/or saffron red powder will confer increased photoabsorption to these other compounds.

Eosins group comprises Eosin Y (tetrabromofluorescein, acid red 87, D&C Red 22) with an abs. max 514-518 nm, stains cytoplasm of cells, collagen, muscle fibers and red blood cells intensely red; and Eosin B (acid red 91, eosin scarlet, dibromo-dinitrofluorescein), with the same staining characteristics as Eosin Y. Eosin Y, eosin B, or a mixture of both can be used because of their sensitivity to the light spectra used: broad spectrum blue light, blue to green light and green light. Their tissue and biofilm staining properties and their low toxicity are also advantageous. Both eosin Y and eosin B stain red blood cells and thus confer to the composition of the present invention haemostatic (controls the flow or stops the flow of blood) properties as well as increase the selective targeting of light to the soft tissues of the lesion or wound during the application of the composition.

Phloxine B (2,4,5,7 tetrabromo 4,5,6,7,tetrachlorofluorescein, D&C Red 28, acid red 92) is a red dye derivative of fluorescein which is used for disinfection and detoxification of waste water through photooxidation. It has an abs. max. of 535-548 nm. It is also used as an intermediate for making photosensitive dyes and drugs.

Erythrosine B (acid red 51, tetraiodofluorescein) is a cherry-pink, coal-based fluorine food dye used as a biological stain, and a biofilm and dental plaque disclosing agent, with max. abs. 524-530 nm in aqueous solution. It is subject to photodegradation. Erythrosine is also used in some embodiments due to its photosensitivity to the light spectra used and its ability to stain biofilms. Inclusion of erythrosine should be favored when using the composition in deep pockets of infected or contaminated tissue, such as periodontal pockets in periodontal therapy.

Rose Bengal (4,5,6,7 tetrachloro 2,4,5,7 tetraiodofluorescein, acid red 94) is a bright bluish-pink biological dye with an absorption max. of 544-549 nm, that has been used as a dye, biological stain and diagnostic aid. Also used in synthetic chemistry to generate singlet from triplet oxygen.

Merbromine (mercurochrome) is an organo-mercuric disodium salt of fluorescein with an abs. max. of 508 nm. It is used as an antiseptic.

Azo Dyes:

The azo (or diazo-) dyes share the N—N group, called azo the group. They are used mainly in analytical chemistry or as food colorings and are not fluorescent. Suitable azo dyes include: Methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), murexide-ammonium purpurate.

Biological Stains:

Dye molecules commonly used in staining protocols for biological materials can also be used as photoactivators. Suitable biological stains include:

Saffranin (Saffranin O, basic red 2) is also an azo-dye and is used in histology and cytology. It Is a classic counter stain in a Gram stain protocol.

Fuchsin (basic or acid) (rosaniline hydrochloride) is a magenta biological dye that can stain bacteria and has been used as an antiseptic. It has an abs. max. 540-555 nm.

3,3' dihexylocarbocyanine iodide (DiOC6) is a fluorescent dye used for staining cell's endoplasmic reticulum, vesicle membranes and mitochondria. It shows photodynamic toxicity; when exposed to blue light, has a green fluorescence.

Carminic acid (acid red 4, natural red 4) is a red glucosidal hydroxyanthrapurin naturally obtained from cochineal insects.

Indocyanin green (ICG) is used as a diagnostic aid for blood volume determination, cardiac output, or hepatic function. ICG binds strongly to red blood cells and when used in mixture with fluorescein, it increases the absorption of blue to green light.

Carotenoids

Carotenoid dyes can also act as photoactivators.

Saffron red powder is a natural carotenoid-containing compound. Saffron is a spice derived from *Crocus sativus*. It is characterized by a bitter taste and iodoform or hay-like fragrance; these are caused by the compounds picrocrocin and saffranal. It also contains the carotenoid dye crocin that gives its characteristic yellow-red color.

Saffron contains more than 150 different compounds many of them are carotenoids: mangicrocin, reaxanthine, lycopene, and various α- and β-carotenes, that show good absorption of light and beneficial biological activity. Also saffron can act as both a photon-transfer agent and a healing factor. Saffron color is primarily the result of α-crocin (8,8 diapo-8,8-carotenoid acid). Dry saffron red powder is highly sensitive to fluctuating pH levels and rapidly breaks down chemically in the presence of light and oxidizing agents. It is more resistant to heat. Data show that saffron has anti-carcinogenic, immunomodulating and antioxidant properties. For absorbance, it is determined for the crocin specific photon wavelength of 440 nm (blue light). It has a deep red colour and forms crystals with a melting point of 186° C. When dissolved in water it forms an orange solution.

Crocetin is another compound of saffron that was found to express an antilipidemic action and promote oxygen penetration in different tissues. More specifically it was observed an increased oxygenation of the endothelial cells of the capillaries. An increase of the oxygenation of muscles and cerebral cortex was observed and led to an increased survival rate in laboratory animals with induced hemorrhagic shock or emphysema.

Anatto a spice contains as main constituent (70-80%) the carotenoid bixin which displayed relevant antioxidative properties.

β-carotene, also displayed suitable characteristics.

Fucoxanthine is a constituent of brown algae with a pronounced ability for photosensitization of red-ox reactions.

Healing Factors:

Healing factors comprise compounds that promote or enhance the healing or regenerative process of the tissues on the application site of the composition. During the photoactivation of the composition, there is an increase of the absorption of molecules at the treatment site by the skin or the mucosa. An augmentation in the blood flow at the site of treatment is observed for an extent period of time. An increase in the lymphatic drainage and a possible change in the osmotic equilibrium due to the dynamic interaction of the free radical cascades can be enhanced or even fortified with the inclusion of healing factors. Suitable healing factors include, but are not limited to:

Hyaluronic acid (Hyaluronan, hyaluronate): is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissues hydrodynamics, movement and proliferation of cells and participates in a wide number of cell surface receptor interactions, notably those including primary receptor CD44. The hyaluronidases enzymes degrade hyaluronan. There are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Current studies evidenced hyaluronic acid appearing in the early stages of healing to physically create room for white blood cells that mediate the immune response. It is used in the synthesis of biological scaffolds for wound healing applications and in wrinkle treatment.

Glucosamine: is one of the most abundant monosaccharides in human tissues and a precursor in the biological synthesis of glycosilated proteins and lipids. It is commonly used in the treatment of osteoarthritis. The common form of glucosamine used is its sulfate salt. Glucosamine shows a number of effects including an anti-inflammatory activity, stimulation of the synthesis of proteoglycans and the synthesis of proteolytic enzymes. A suitable range of concentration over which glucosamine can be used in the present composition is from about 1% to about 3%.

Allantoin: is a diureide of glyosilic acid. It has keratolytic effect, increases the water content of the extracellular matrix, enhances the desquamation of the upper layers of dead (apoptotic) skin cells, and promotes skin proliferation and wound healing.

Also, saffron can act as both a photon-transfer agent and a healing factor.

Chelating Agents:

Chelating agents can be included to promote smear layer removal in closed infected pockets and difficult to reach lesions; act as a metal ion quencher and as a buffer. Suitable chelating agents include, but are not limited to:

Ethylenediaminetetraacetic acid (EDTA): It is an aminoacid, used to sequester di- and trivalent metal ions. EDTA binds to metals via 4 carboxylate and 2 amine groups. EDTA forms especially strong complexes with Mn(III), Fe(III), Cu(III), Co(III). Prevents collection of the platelets and blood clots formation. It is used in the endodontic therapy as a smear layer removal agent during instrumentation. It is used to buffer solutions.

Ethylene glycol tetraacetic acid (EGTA) is related to EDTA, but with a much higher affinity for calcium than for magnesium ions. It is useful for making buffer solutions that resemble the environment inside living cells and is often employed in dentistry, more specifically endodontics, in the removal of smear layer.

Lipolysis Stimulating Factors:

Lipolysis stimulating factors can be included for use of the composition in cosmetic applications, such as wrinkle treatment.

Caffeine, and the metabolic derivative of caffeine paraxanthine can increase in the lipolysis process to releases glycerol and fatty acids into the blood stream.

Hydrophilic Gelling Agents

The skin rejuvenation composition may also contain one or more hydrophilic gelling agent. The hydrophilic gelling agent enhances the consistency of the composition and contributes to facilitating the application of the composition to the skin or wounded area. Also, when used with hydrogen peroxide ($H_2O_2$), it may contribute to the slow the release of the $H_2O_2$, and provide a more immediate reaction because pure $H_2O_2$ can be used directly. Suitable hydrophilic gelling agent include, but are not limited to glucose, modified starch, methyl cellulose, carboxymethyl cellulose, propyl cellulose, hydroxypropyl cellulose, Carbopol® polymers, alginic acid, sodium alginate, potassium alginate, ammonium alginate, calcium alginate, agar, carrageenan, locust bean gum, pectin, and gelatin.

Use of the Composition

The inclusion of suitable photosensitive compounds and activation with a light source of a proper wavelength, leads to the acceleration in the breakdown process of the source of peroxide (the oxidant) and the other reactions that take place, via a photodynamic phenomenon. The included dyes are illuminated by photons of a certain wavelength and excited to a higher energy state. When the photoactivators' excited electrons return to a lower energy state, they emit photons with a lower energy level, thus causing the emission of light of a longer wavelength (Stokes shift). In the proper environment, much of this energy transfer is transferred to oxygen or the reactive hydrogen peroxide and causes the formation of oxygen radicals, such as singlet oxygen.

The singlet oxygen and other reactive oxygen species generated by the activation of the composition are thought to operate in a hormetic fashion. That is, a health beneficial effect is brought about by the low exposure to a normally toxic stimuli (e.g. reactive oxygen), by stimulating and modulating stress response pathways in cells of the targeted tissues. Endogenous response to exogenous generated free radicals (reactive oxygen species) is modulated in increased defense capacity against the exogenous free radicals and induces acceleration of healing and regenerative processes. Furthermore, activation of the composition will also produce an antibacterial effect. The extreme sensitivity of bacteria to exposure to free radicals makes the composition of the present invention a de facto bactericidal composition.

Possible mechanism of action should be a fortified redox signaling phenomenon resulting in accentuated signal transduction process in which cells convert one kind of signal into another; activated "second messengers" induce a "signal cascade" beginning with a relatively small stimulus that elicits a large response via biologically monitored amplification of such signals. These complex mechanisms act possibly involving angiogenic phenomena via growth factor activation.

This method could be described as a form of photodynamic therapy. However, unlike other photodynamic techniques, where the photoactoactivators are incorporated in the tissue structure, in the present method, the photoactive material is in simple contact with the tissue and acts when activated by light, as a "photodynamic device" that chemically interacts with the tissue. Additionally, the actinic light penetrates the tissue, and the light that is emitted by the photoactivator (light of a longer wavelength) is also absorbed by the tissue.

Any source of actinic light can be used. Any type of halogen, LED or plasma arc lamp, or laser may be suitable. The primary characteristic of suitable sources of actinic light will be that they emit light in a wavelength (or wavelengths) appropriate for activating the one or more photoactivators present in the composition. In one embodiment, an argon laser is used. In another embodiment, a potassium-titanyl phosphate (KTP) laser (e.g. a Greenlight™ laser) is used. In yet another embodiment, a LED photocuring device is the source of the actinic light. In yet another embodiment, the source of the actinic light is a source of visible light having a wavelength between 400 and 600 nm. Furthermore, the source of actinic light should have a suitable power density. Suitable power density for non-collimated light sources (LED, halogen or plasma lamps) are in the range from about 900 mW/cm$^2$ to about 2000 mW/cm$^2$. Suitable power density for laser light sources are in the range from about 0.5 mW/cm$^2$ to about 0.8 mW/cm$^2$.

The duration of the exposure to actinic light will be dependent on the surface of the treated area, and on the type of lesion, trauma or injury that is being treated. The photoactivation of the composition may take place within seconds or even fragment of seconds, but a prolonged exposure period is beneficial to exploit the synergistic effects of the absorbed, reflected and reemitted light on the composition of the present invention and its interaction with the tissue being treated. In one embodiment, the time of exposure to actinic light of the tissue, skin or wound on which the skin rejuvenation composition has been applied is a period between 60 second and 5 minutes. In another embodiment, the time of exposure to actinic light of the tissue, skin or wound on which the skin rejuvenation composition has been applied is a period between 60 seconds and 5 minutes per $cm^2$ of the area to be treated, so that the total time of exposure of a 10 $cm^2$ are would be between 10 minutes and 50 minutes. In yet another embodiment, the source of actinic light is in continuous motion over the treated area for the appropriate time of exposure. In yet another embodiment, multiple applications of the skin rejuvenation composition and actinic light are performed. In some embodiments, the tissue, skin or wound is exposed to actinic light at least two, three, four, five or six times. In some embodiments, a fresh application of the skin rejuvenation composition is applied before exposure to actinic light.

Alternative Embodiments

Example I

An exemplary skin rejuvenation composition was prepared by mixing the following components:

| Oxidant | Photoactivators | Healing factor(s) |
| --- | --- | --- |
| Carbamide peroxide (16%) | Erythrosine B (0.5%) Eosin B (0.25%) Saffron Red powder (0.25%) | Glucosamine sulfate (3%) Hyaluronic acid (3%) |

The oxidant (4 mL) and healing factors (1.5 mL) were mixed and the combined with the photoactivators (1 mL). The resulting composition was applied to the skin of a patient, and activated with actinic light provided by a LED photocuring device (blue light). The composition was removed following treatment.

Example II

An second exemplary skin rejuvenation composition was prepared by mixing the following components:

| Oxidant | Photoactivators | Healing factor(s) |
| --- | --- | --- |
| Carbamide peroxide (16%) | Fluorescein Indocyanin green Saffron Red powder (0.25%) | Glucosamine sulfate (3%) Hyaluronic acid (3%) |

The oxidant (4 mL) and healing factors (1.5 mL) were mixed and the combined with the photoactivators (1 mL). The resulting composition was applied to the skin of a patient, and activated with actinic light provided by a LED photocuring device (blue light). The composition was removed following treatment.

This second exemplary composition is using the fluorescein dye as a photoactivator to other dyes (indocyanine green and saffron red powder) present in the composition. The addition of a small amount of fluorescein to the indocyanine green and saffron red powder solution caused reemission of light at wavelengths that activated the other dye compounds and improved the treatment by increasing the established clinical absorption/reemission criteria.

Indocyanine green binds well to hemoglobin and helps selective energy absorption by the tissues and also helps targeting these tissues with the generated free radical cascades. Also, this photoactivators mixture is able to render saffron red fluorescent, which again improves both the photodynamic and biostimulating phenomena.

Example III

Figure 2:
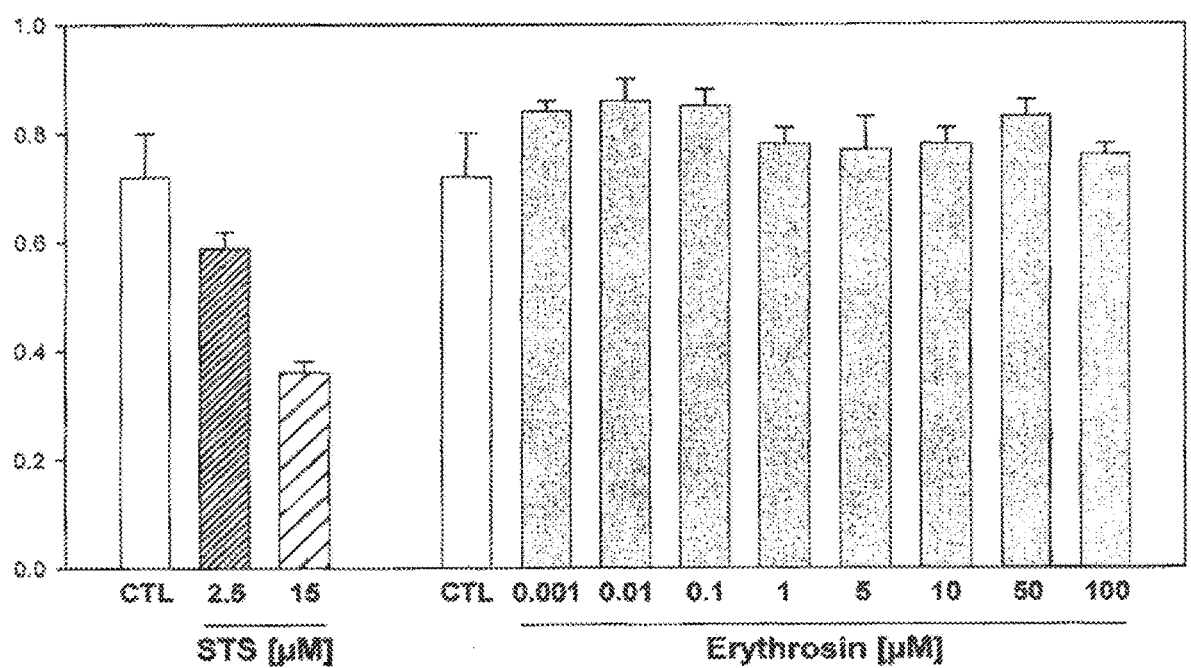
FIG. 2 illustrates that Erythrosine B does not affect cellular viability. Hep G2 cells were treated for 24 hours with increasing concentrations (0.001 to 100 μM) of Erythrosine B, or left untreated (CTL). Staurosporine (STS) was used as a positive control inducing cellular mortality. Higher concentrations (0.5 and 1 mM) of Erythrosine B could not be tested as the dye interfered with the assay.

The toxicity of the photoactivators Eosin Y and Erythrosine B was evaluated by measuring the cytotoxicity of these compounds on human cells. Hep G2 human hepatocellular carcinoma cells with an epithelial morphology were treated for 24 hours with increasing concentrations (0.001 to 100 μM) of Eosin Y or Erythrosine B, and the cellular survival was evaluated. Increasing concentrations of either Eosin Y (FIG. 1) or Erythrosine B (FIG. 2) did not affect cellular viability when compared to untreated cells. Staurosporine (STS) was used as a positive control for inducing cellular mortality and caused a dose-dependent effect (FIGS. 1 and 2). Similar results were obtained by measuring cell death by release of lactate dehydrogenase (LDH). Therefore, neither Eosin Y or Erythrosine B caused increased cellular mortality.

Example IV

Skin Rejuvenation in an Animal Model

Several studies of photodynamic technology (PDT) have shown stimulatory effects of PDT on cell types, especially the formation of collagen precursor and enzymes associated with cellular development. The present invention offers means of skin rejuvenation which can be used to treat large surface areas with no significant adverse effects.

A study was performed in Wistar rats to evaluate the effects of the composition of the present invention in the presence of light in an animal skin model, using a skin flap model. Using a template of 3 cm by 9 cm (3×9) in plexiglas, a flap was traced on the dorsal skin with a surgical marker, taking as limits the inferior angles of the scapulae and the superior bones of pelvis. A pure random pattern flap with cranial base was cut using sterile techniques and elevated through deep fascia, including superficial fascia, panniculus carnosus, the subcutaneous tissue and skin. To minimize skin contraction and simulating the human skin, a 0.5 cm subcutaneous layer of panniculus carnosus from the wound edges was removed. During one hour, an impermeable barrier (e.g. a silicone sheeting) was placed between the flap and its donor site to eliminate the possibility of wound bed support. The sheet was then removed, the flap returned to its original position and the flap edges were surgically closed using 4/0 nylon suture in an interrupted fashion. Immediately following flap closure, flap pedicle were coated with 13.5 g of gel formulation (0.5 $g/cm^2$) and irradiated. The controls did not receive any treatment. Care was taken to distribute ointment evenly along the entire flap. Gel formulation was prepared the same day of the experiment. For Gel+Light group the animals were treated with gel formulation, the flap was irradiated for 3 minutes with a LED lamp.

Figure 3:
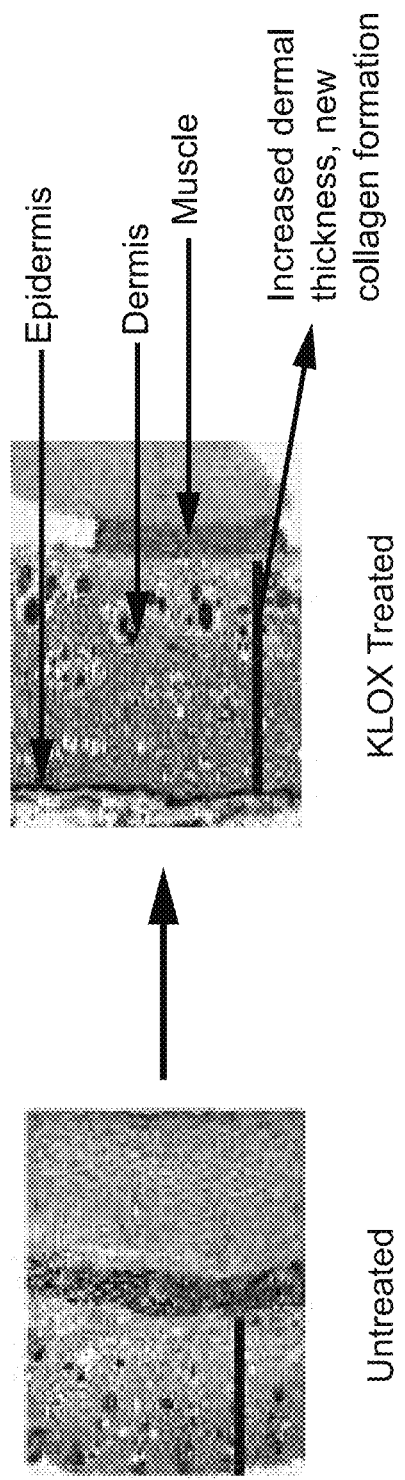
FIG. 3. Illustrates a transversal view of rat skin treated or not with the composition according to the present invention in conjunction with exposure to light.

Now referring to FIG. 3, the results show increased dermal thickness and new collagen formation on skin treated with the composition of the present invention versus untreated skin. These result support the role of the composition of the present invention in the stimulation of better outcomes in the skin rejuvenation process.

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

The invention claimed is:

1. A method for reversing or mitigating skin aging comprising:
   a) topically applying on an area of a patient's skin to be treated a composition comprising at least one oxidant selected from at least one of hydrogen peroxide, carbamide peroxide and benzoyl peroxide, and at least one fluorescent dye selected from a xanthene derivative dye, an azo dye, a biological stain and a cartenoid, capable of activating the oxidant;
   b) illuminating the applied composition with actinic light for a period of about 60 seconds to about 5 minutes per cm$^2$ of the area to be treated; thereby reversing or mitigating skin aging; and c) at least one healing factor selected from hyaluronic acid, glucosamine and allantoin.

2. The method according to claim 1, wherein the actinic light has an emission wavelength of between about 400 nm and about 600 nm.

3. The method according to claim 1, wherein the actinic light has a power density of between about 900 mW/cm$^2$ to about 2000 mW/cm$^2$.

4. The method according to claim 1, wherein the actinic light is in continuous motion over an area to be treated.

5. The method according to claim 1, wherein the composition further comprises at least one hydrophilic gelling agent.

6. The method according to claim 5, wherein the at least one hydrophilic gelling agent is selected from at least one of glucose, modified starch, methyl cellulose, carboxymethyl cellulose, propyl cellulose, hydroxypropyl cellulose, a carbomer polymer, alginic acid, sodium alginate, potassium alginate, ammonium alginate, calcium alginate, agar, carrageenan, locust bean gum, pectin and gelatin.

7. The method according to claim 1, wherein the composition further comprises at least one chelating agent selected from ethylenediaminetetraacetic acid (EDTA) an ethylene glycol tetraacetic acid (EGTA).

8. The method according to claim 1, wherein the composition further comprises at least one of rhodamine B, rhodamine WT, rhodamine G, phloxine B, rose bengal, eosin B, fluorescein, Erythrosine B, saffranin O, basic fuchsine, acid fuchsine, 3,3'-dihexylocarbocyanine iodide, carminic acid, indocyanine green, crocetin, alpha-crocin (8,8-diapo-8,8-carotenoic acid), zeaxanthine, lycopene, alpha-carotene, beta-carotene, merbromine, bixin, fucoxanthine, methyl violet, neutral red, para red, amaranth, carmoisine, allura red AC, tartrazine, orange G, ponceau 4R, methyl red, murexide-ammonium purpurate, pyronine Y and pyronine B.

9. The method according to claim 1, wherein the composition further comprises at least one lipolysis stimulating factor selected from caffeine and paraxanthine.

* * * * *